US012060312B2

(12) United States Patent
Tsuda et al.

(10) Patent No.: US 12,060,312 B2
(45) Date of Patent: Aug. 13, 2024

(54) PRODUCTION METHOD FOR ISOCYANATE COMPOUND

(71) Applicants: NATIONAL UNIVERSITY CORPORATION KOBE UNIVERSITY, Hyogo (JP); AGC Inc., Tokyo (JP)

(72) Inventors: Akihiko Tsuda, Hyogo (JP); Takashi Okazoe, Tokyo (JP)

(73) Assignees: NATIONAL UNIVERSITY CORPORATION KOBE UNIVERSITY, Hyogo (JP); AGC INC., Tokyo (JP)

( * ) Notice: Subject to any disclaimer, the term of this patent is extended or adjusted under 35 U.S.C. 154(b) by 671 days.

(21) Appl. No.: 17/292,582

(22) PCT Filed: Nov. 14, 2019

(86) PCT No.: PCT/JP2019/044666
§ 371 (c)(1),
(2) Date: May 10, 2021

(87) PCT Pub. No.: WO2020/100971
PCT Pub. Date: May 22, 2020

(65) Prior Publication Data
US 2022/0002234 A1    Jan. 6, 2022

(30) Foreign Application Priority Data

Nov. 15, 2018 (JP) .................................. 2018-214988

(51) Int. Cl.
| | | |
|---|---|---|
| *C07C 263/10* | (2006.01) | |
| *B01J 19/00* | (2006.01) | |
| *B01J 19/12* | (2006.01) | |
| *C08G 18/76* | (2006.01) | |

(52) U.S. Cl.
CPC ......... *C07C 263/10* (2013.01); *B01J 19/0013* (2013.01); *B01J 19/123* (2013.01); *C08G 18/7671* (2013.01)

(58) Field of Classification Search
CPC ... B01J 19/0013; B01J 19/123; C07C 263/00; C07C 263/10; C07C 265/04; C07C 265/10; C07C 265/12; C07C 269/02; C07C 271/20; C07C 271/28; C07C 319/20; C07C 323/25; C08G 18/282; C08G 18/3206; C08G 18/4825; C08G 18/7671; A45C 11/00; A45C 2011/003; G06F 1/1626; G06F 1/1628; H01G 2/065; H01G 2/14; H01G 4/012; H01G 4/12; H01G 4/1227; H01G 4/1236; H01G 4/224; H01G 4/228; H01G 4/232; H01G 4/2325; H01G 4/248; H01G 4/30; H01G 4/38; G06Q 10/063112; G06Q 30/0619; G06Q 30/08
See application file for complete search history.

(56) References Cited

U.S. PATENT DOCUMENTS

2018/0354894 A1   12/2018   Miyamoto et al.

FOREIGN PATENT DOCUMENTS

| EP | 0364765 | * | 4/1990 |
| EP | 1020435 | * | 7/2000 |
| JP | 2013-181028 | | 9/2013 |
| JP | 2013181028 | * | 9/2013 |
| WO | 2015/156245 | | 10/2015 |
| WO | 2017/104709 | | 6/2017 |

OTHER PUBLICATIONS

JP2013181028 translated 7 pages (Year: 2013).*
EP0364765 translated 20 pages (Year: 1990).*
Office Action issued Dec. 15, 2022 in corresponding Chinese Patent Application No. 201980074693.X, with English language translation.
Notice of Reasons for Refusal issued Sep. 19, 2023 in corresponding Japanese Patent Application No. 2020-556160, with English language translation.
Chinese Office Action issued Jul. 1, 2022 in corresponding Chinese Office Action No. 201980074693.X, with English translation.
Extended European Search Report issued Jul. 11, 2022 in corresponding European Application No. 19883776.7.
International Search Report issued Jan. 28, 2020 in International (PCT) Application No. PCT/JP2019/044666.
Irie et al., "Production of Phosgen", Journal of the Fuel Society of Japan, 1960, vol. 39, No. 400, pp. 575-583, with partial English Translation.
Alapi et al., "Direct VUV photolysis of chlorinated methanes and their mixtures in an oxygen stream using an ozone producing low-pressure mercury vapour lamp", Chemosphere, 2007, vol. 67, pp. 693-701.
Kawai et al., "Discussion on Decomposition of Chloroform", Yakugaku Zasshi, 1996, vol. 86, No. 12, pp. 1125-1132, with partial English Translation.
Kuwahara et al., "Photochemical molecular storage of $Cl_2$, HCl, and $COCl_2$: Synthesis of organochlorine compounds, salts, ureas, and polycarbonate with photodecomposed chloroform", Org. Lett., 2012, vol. 14, No. 13, pp. 3376-3379.

(Continued)

Primary Examiner — Yevgeny Valenrod
Assistant Examiner — Blaine G Doletski
(74) Attorney, Agent, or Firm — Wenderoth, Lind & Ponack, L.L.P

(57) ABSTRACT

The objective of the present invention is to provide a method for producing an isocyanate compound safely and efficiently. The method for producing an isocyanate compound according to the present invention is characterized in comprising the steps of irradiating a high energy light to a halogenated methane at a temperature of 15° C. or lower in the presence of oxygen, and further adding a primary amine compound to be reacted without irradiating a high energy light.

10 Claims, 1 Drawing Sheet

(56) References Cited

OTHER PUBLICATIONS

Hautecloque et al., "On the photooxidation of gaseous $HCCl_3$ and ClO radical formation", Journal of Photochemisty, 1980, vol. 14, pp. 157-165.

Chinese Decision of Rejection issued Jun. 29, 2023 in corresponding Chinese Patent Application No. 201980074693.X, with English translation.

* cited by examiner

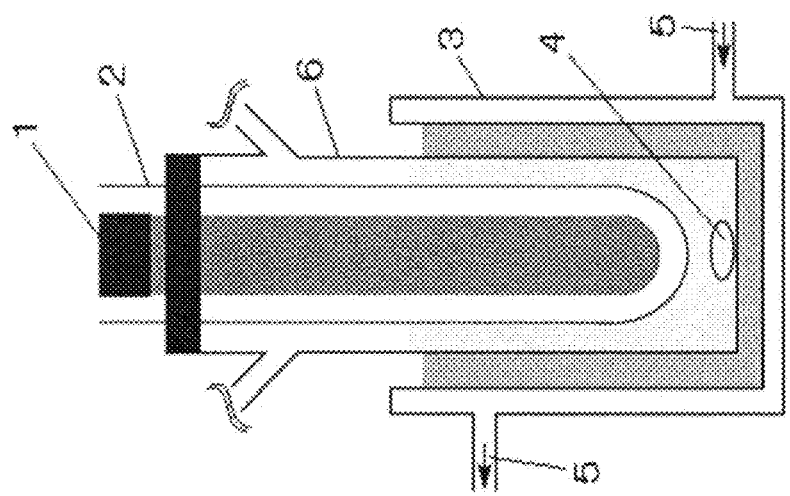

PRODUCTION METHOD FOR ISOCYANATE COMPOUND

TECHNICAL FIELD

The present invention relates to a method for producing an isocyanate compound safely and efficiently, and a method for producing a polyurethane using the above method.

BACKGROUND ART

An isocyanate compound having an isocyanate group, "—N=C=O", is highly reactive and very useful as a raw material for a polyurethane or the like. An isocyanate compound is generally synthesized by reacting an amine compound and phosgene (Patent document 1).

Phosgene is however very toxic. For example, phosgene is easily reacted with water to generate hydrogen chloride and has a history of being used as poisonous gas. Phosgene is generally produced by a high-heat-generating gas-phase reaction between anhydrous chlorine gas and highly pure carbon monoxide in the presence of an activated carbon catalyst. Chlorine gas and carbon monoxide used in this reaction are also toxic. The basic process to produce phosgene has not significantly changed since the 1920s. The production of phosgene by such a process requires an expensive and huge facilities. In addition, it is essential for plant design to ensure a wide range of safety due to high toxicity of phosgene. Thus, the production cost increases. Furthermore, a large-scale process to produce phosgene may cause many environmental problems. Alternatively, phosgene is produced by decomposing triphosgene with using a base such as triethylamine, but triphosgene is an expensive reagent. It is also known that triphosgene has a potential risk of breakdown into phosgene by some physical stimulus or chemical stimulus and triphosgene itself is highly toxic.

The inventor of the present invention has developed a method for producing a compound such as phosgene by irradiating a light to a halogenated hydrocarbon in the presence of oxygen (Patent document 2). Patent document 2 discloses a method in which the generated compound is supplied to another reaction vessel and a method in which a halogenated hydrocarbon and a raw material compound are allowed to coexist and the generated compound is reacted with the raw material compound in one reaction vessel.

Also, the present inventor has developed a method for producing a halogenated carbonate ester by irradiating a light to a mixture containing a halogenated hydrocarbon and an alcohol in the presence of oxygen (Patent document 3).

PRIOR ART DOCUMENT

Patent Document

Patent document 1: WO 2017/104709
Patent document 2: JP 2013-181028 A
Patent document 3: WO 2015/156245

DISCLOSURE OF THE INVENTION

Problems to be Solved by the Invention

The present inventor has developed a method to utilize phosgene more safely as described above. For example, however, when a primary amine compound is used as a raw material compound in the method described in Patent document 2, an isocyanate compound cannot be obtained, since the reaction proceeds to obtain a urea derivative and a polyurea.

A generation of a carbonate is suppressed and a halogenated formate ester is obtained in the method described in Patent document 3 by using a relatively small amount of an alcohol to a halogenated hydrocarbon. Though an alcohol compound is used as a raw material compound in Patent document 3, it is not suggested to use a primary amine compound.

The objective of the present invention is to provide a method for producing an isocyanate compound safely and efficiently, and a method for producing a polyurethane using the above method.

Means for Solving the Problems

The inventor of the present invention repeated intensive studies in order to solve the above-described problems. It was conventionally thought that phosgene is not produced at low temperature, since heat is needed in addition to a light to obtain phosgene by decomposing a halogenated methane. In addition, it was thought that phosgene is easily decomposed by an irradiation of a light in the presence of a large amount of oxygen to generate carbon monoxide, carbon dioxide, chlorine and the like. On the one hand, the present inventor experimentally found that phosgene is surprisingly generated at relatively low temperature and generated phosgene is not readily decomposed. In addition, there is little concern that phosgene is leaked out of a reaction system under relatively low temperature, since the boiling point of phosgene at an ordinary pressure is 8.3° C. The present inventor completed the present invention by finding that an isocyanate compound can be produced safely and efficiently by producing a halogenated carbonyl compound at relatively low temperature and adding a primary amine compound thereto.

The present invention is hereinafter described.

[1] A method for producing an isocyanate compound, the method comprising the steps of:
irradiating a high energy light to a halogenated methane at a temperature of 15° C. or lower in the presence of oxygen, and
adding a primary amine compound to be reacted without irradiating a high energy light.

[2] The method for producing the isocyanate compound according to the above [1], wherein the temperature is 5° C. or lower.

[3] The method for producing the isocyanate compound according to the above [1] or [2], wherein a base is added in addition to the amine compound.

[4] The method for producing the isocyanate compound according to the above [3], wherein the base is an organic base.

[5] The method for producing the isocyanate compound according to the above [4], wherein the organic base is one or more heterocyclic aromatic amines selected from pyridine, picoline and lutidine.

[6] The method for producing the isocyanate compound according to the above [4], wherein the organic base is one or more non-nucleophilic strong bases selected from 1,5,7-triazabicyclo[4.4.0]dec-5-ene, 7-methyl-1,5,7-triazabicyclo[4.4.0]dec-5-ene, 1,8-diazabicyclo[5.4.0]undec-7-ene, 1,5-diazabicyclo[4.3.0]non-5-ene and 1,1,3,3-tetramethylguanidine.

[7] The method for producing the isocyanate compound according to any one of the above [1] to [6], wherein the high energy light comprises a light having a wavelength of 180 nm or more and 280 nm or less.

[8] The method for producing the isocyanate compound according to any one of the above [1] to [7], wherein a halogeno group in the halogenated methane is one or more halogeno groups selected from chloro, bromo and iodo.

[9] The method for producing the isocyanate compound according to the above [8], the halogenated methane is chloroform.

[10] A method for producing a polyurethane, the method comprising the steps of:

producing a polyisocyanate compound having two or more isocyanate groups by the method according to any one of the above [1] to [9], and adding a polyol compound to a reaction mixture of the above step comprising the polyisocyanate compound.

Effect of the Invention

A highly toxic compound and an expensive catalyst as a raw material compound, such as phosgene and carbon monoxide, are not needed to be used in the present invention method. In addition, phosgene is less relatively likely to be leaked out of the reaction system, an isocyanate compound can be obtained with high yield, and eventually a polyurethane or the like can be efficiently produced from the obtained isocyanate compound. Thus, the present invention method is industrially very useful as a technology to safely and efficiently produce a useful isocyanate compound.

BRIEF DESCRIPTION OF THE DRAWINGS

The FIGURE is a schematic diagram to demonstrate one example of the constitution of a reaction apparatus usable in the present invention method.

MODE FOR CARRYING OUT THE INVENTION

1. Halogenated Methane Decomposition Step

A halogenated carbonyl or a halogenated carbonyl-like compound is obtained in this step by irradiating a high energy light to a halogenated methane at a temperature of 15° C. or lower in the presence of oxygen to decompose the halogenated methane.

A halogenated methane may be decomposed to be transformed to a halogenated carbonyl or a halogenated carbonyl-like compound, such as phosgene, in the reaction of the present invention by a high energy light and oxygen. For example, strict regulations are imposed on the transportation or the like of phosgene, since phosgene as a halogenated carbonyl is very highly toxic. On the one hand, a halogenated methane is not obviously so dangerous.

A halogenated methane that is liquid under an atmospheric temperature and an atmospheric pressure is particularly used as an organic solvent or the like in a large amount but causes environmental pollution such as air pollution and ozone layer destruction when released to the atmosphere. The present invention is a technology to produce a useful compound by a photolysis of a halogenated methane and greatly contributes to both an industry and an environmental science.

The halogenated methane is a methane that is substituted by one or more halogeno groups selected from the group consisting of fluoro, chloro, bromo and iodo, preferably a methane that is substituted by one or more halogeno groups selected from the group consisting of chloro, bromo and iodo. A part of the halogenated methane may be decomposed by a high energy light and oxygen and may act similarly to a halogenated carbonyl in the present invention as described above.

An example of the halogenated methane specifically includes a fluoromethane such as trifluoromethane; a chloromethane such as dichloromethane, chloroform and carbon tetrachloride; a bromomethane such as dibromomethane and bromoform; an iodomethane such as iodomethane and diiodomethane; and chlorodifluoromethane, dichlorofluoromethane, trichlorofluoromethane and bromofluoromethane.

The halogenated methane may be appropriately selected depending on the target reaction and the desired product. One of the halogenated methane may be used by itself, or two or more of the halogenated methanes may be used in combination. It is preferred that only one kind of the halogenated methane is used depending on the target compound. The halogenated methane having chloro is preferred.

The halogenated methane usable in the present invention method may be a halogenated methane that has been once used as, for example, a solvent. It is preferred that such a used halogenated methane is purified to some extent for use, since the reaction may be possibly inhibited when a large amount of an impurity and water are contained. For example, it is preferred that water and a water-soluble impurity are removed by washing with water and then the halogenated methane is dried over anhydrous sodium sulfate, anhydrous magnesium sulfate or the like. On the one hand, an excessive purification by which the productivity becomes less is not needed, since the reaction to decompose the halogenated methane may proceed even when water is contained. The water content is preferably 0 mass % or more, more preferably 0.0001 mass % or more, and preferably 0.5 mass % or less, more preferably 0.2 mass % or less, even more preferably 0.1 mass % or less. The recycled halogenated methane may contain a degradant of the halogenated methane.

The phrase "in the presence of oxygen" in this disclosure means any one of the state that the halogenated methane is contacted with oxygen and the state that there is oxygen in the halogenated methane. The reaction of this step may be carried out under a stream of a gas containing oxygen but it is preferred to supply a gas containing oxygen into the halogenated methane by bubbling in terms of a high decomposition efficiency of the halogenated methane.

An oxygen source may be a gas containing oxygen, and for example, air or purified oxygen may be used. Purified oxygen may be mixed with an inert gas such as nitrogen and argon to be used. It is preferred to use air in terms of cost and easiness. An oxygen content in the gas used as an oxygen source is preferably about 15 vol % or more and about 100 vol % or less in terms of high decomposition efficiency of the halogenated methane by high energy light irradiation. The oxygen content may be appropriately determined depending on the kind of the halogenated methane or the like. For example, when a halogenated methane such as dichloromethane and chloroform is used as the halogenated methane, the oxygen content is preferably 15 vol % or more and 100 vol % or less. When a bromomethane such as dibromomethane and bromoform is used, the oxygen content is preferably 90 vol % or more and 100 vol % or less. Even when oxygen having an oxygen content of 100 vol % is used, the oxygen content can be controlled in the above-described range by adjusting a flow rate of oxygen into the reaction system. A manner to supply a gas containing oxygen is not particularly restricted, and the gas may be supplied into the reaction system from an oxygen tank equipped with a flow rate adjustor or from an oxygen generating device.

An amount of an oxygen-containing gas may be appropriately determined depending on the amount of the halogenated methane or a shape of a reaction vessel. For example, an amount of the gas supplied to a reaction vessel per 1 minute to the halogenated methane in the reaction vessel is preferably 5 times or more by volume. The ratio is more preferably 10 times or more by volume, and even more preferably 25 times or more by volume. The upper limit of the ratio is not particularly restricted, and the ratio is preferably 500 times or less by volume, more preferably 250 times or less by volume, and even more preferably 150 times or less by volume. The amount of oxygen supplied to a reaction vessel per 1 minute to the halogenated methane in the reaction vessel may be adjusted to 1 time or more by volume and 25 times or less by volume. When an amount of the gas is excessively large, the halogenated methane may be possibly volatilized, but when the amount is excessively small, it may possibly become difficult to promote the reaction. For example, a supply rate of oxygen may be 0.01 L/min or more and 10 L/min or less per 4 mL of the halogenated methane.

The halogenated methane is contacted with oxygen at 15° C. or lower in the present invention. For example, the boiling point of phosgene as a halogenated carbonyl under an atmospheric pressure is 8.3° C.; therefore, even when phosgene is generated, phosgene may not be leaked out from the halogenated methane at 15° C. or lower. The temperature is preferably 10° C. or lower and more preferably 5° C. or lower or 2° C. or lower in terms of the leakage difficulty of a halogenated carbonyl and a halogenated carbonyl-like compound. The lower limit of the temperature is not particularly restricted, and for example, the temperature is preferably −80° C. or higher and more preferably −20° C. or higher or −15° C. or higher.

The high energy light irradiated to the halogenated methane means a light that has an energy enough to decompose the halogenated methane. For example, a light containing UV-B having a wavelength of 280 nm or more and 315 nm or less and/or UV-C having a wavelength of 180 nm or more and 280 nm or less may be used, a light containing UV-C having a wavelength of 180 nm or more and 280 nm or less is preferably used, a light having a peak wavelength included in the range of 180 nm or more and 315 nm or less is more preferred, and a light having a peak wavelength included in the range of 180 nm or more and 280 nm or less is even more preferred. A wavelength or a peak wavelength of the high energy light may be appropriately determined depending on the kind of the halogenated methane, and is more preferably 400 nm or less and even more preferably 300 nm or less. When the irradiated light contains a light of the above-described wavelength range, the halogenated methane can undergo oxidative photodecomposition in an efficient fashion. For example, the light containing UV-B having a wavelength of 280 nm or more and 315 nm or less and/or UV-C having a wavelength of 180 nm or more and 280 nm or less or the light having a peak wavelength included in the ranges can be used, and the light containing UV-C having a wavelength of 180 nm or more and 280 nm or less or the light having a peak wavelength included in the range is preferably used. Sunlight contains a certain percentage of ultraviolet and fluorescent light contains few ultraviolet but UV-C is not contained in fluorescent light and the sunlight that reaches the surface of the earth and the lights do not have energy enough to decompose the halogenated methane; therefore, the lights are not included in the high energy light of the present invention.

A means for the light irradiation is not particularly restricted as long as the light having the above-described wavelength can be irradiated by the means. An example of a light source containing a sufficient amount of the light in the wavelength range includes sunlight, low pressure mercury lamp, medium pressure mercury lamp, high pressure mercury lamp, ultrahigh pressure mercury lamp, chemical lamp, black light lamp, metal halide lamp and LED lamp. A low pressure mercury lamp is preferably used in terms of a reaction efficiency and a cost.

The conditions such as a strength of the light to be irradiated or the like may be appropriately determined depending on the kind and usage amount of the raw material compounds. For example, a light strength at a shortest distance position of the composition from the light source is preferably 1 mW/cm$^2$ or more and 50 mW/cm$^2$ or less. A shortest distance between the light source and the halogenated methane is preferably 1 m or less, more preferably 50 cm or less, and even more preferably 10 cm or less or 5 cm or less. The lower limit of the shortest distance is not particularly restricted and may be 0 cm, in other words, the light source may be immersed into the halogenated methane.

A reaction apparatus usable in the present invention method is exemplified by a reaction vessel equipped with a high energy light irradiation means. A reaction apparatus may be equipped with a stirring device and a temperature control means. One embodiment of a reaction apparatus usable in the present invention method is shown in the FIGURE. The reaction apparatus shown in the FIGURE has a high energy light irradiation means 1 in a cylindrical reaction vessel 6. The halogenated methane is added into a cylindrical reaction vessel 6, and a high energy light is irradiated by using a high energy light irradiation means 1 while a gas containing oxygen is supplied into the cylindrical reaction vessel 6 or a gas containing oxygen is blown into the composition to cause bubbling (not shown in the Figure) for the reaction. When a high energy light irradiation means 1 is covered with a jacket 2 or the like, it is preferred that the jacket is composed of a material that allows passing the high energy light. A high energy light may be irradiated from outside a reaction vessel. In such a case, the reaction vessel is composed of a material that allows passing the high energy light. A material that allows passing the high energy light is not particularly restricted as long as the effect of the present invention is not inhibited, and is preferably exemplified by quartz glass.

A time to irradiate a high energy light may be appropriately adjusted in the range in which the halogenated methane is sufficiently decomposed, and is preferably 0.5 hours or more and 10 hours or less, more preferably 1 hour or more and 6 hours or less, and even more preferably 2 hours or more and 4 hours or less. A manner to irradiate the high energy light is not also particularly restricted, and any manners can be selected. For example, the high energy light may be continuously irradiated from the reaction initiation to the reaction completion, irradiation and un-irradiation of the high energy light may be alternately repeated, and the high energy light may be irradiated from the reaction initiation for a predetermined time only. The embodiment to continuously irradiate the high energy light from the reaction initiation to the reaction completion is preferred.

2. Isocyanate Compound Generation Step

An isocyanate compound is obtained by further adding a primary amine compound to the halogenated methane after a high energy light is irradiated and reacting with a degradant of the halogenated methane without irradiating a high energy light in one embodiment of the present invention. The degradant of the halogenated methane means a halogenated carbonyl or a halogenated carbonyl-like compound. The halogenated carbonyl-like compound is not completely same as the halogenated carbonyl but is a compound similar to the halogenated carbonyl. The halogenated carbonyl-like compound means a compound that acts similarly to the halogenated carbonyl and reacts with a primary amine to generate an isocyanate compound.

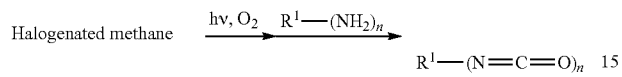

The primary amine compound is not particularly restricted as long as the compound has one or more amino groups, "—$NH_2$ group". In the above formula, the $R^1$ in the primary amine compound: $R^1$—$(NH_2)_n$ is an n-valent organic group. An example of the organic group includes a $C_{1-15}$ chain aliphatic hydrocarbon group, a $C_{3-15}$ cyclic aliphatic hydrocarbon group, a $C_{6-15}$ aromatic hydrocarbon group and a group formed by connecting 2 or more and 5 or less of the groups. The "n" is an integer of 1 or more and 6 or less, preferably 5 or less, 4 or less or 3 or less, more preferably 1 or 2, and even more preferably 2.

The "$C_{1-15}$ chain aliphatic hydrocarbon group" means a linear or branched saturated aliphatic hydrocarbon group having a carbon number of 1 or more and 15 or less. An example of a $C_{1-15}$ divalent chain aliphatic hydrocarbon group includes a $C_{1-15}$ alkylene group, a $C_{2-15}$ alkenylene group and a $C_{2-15}$ alkynylene group.

An example of the $C_{1-15}$ alkylene group includes methylene, ethylene, n-propylene, isopropylene, n-butylene, 1-methylpropylene, 2-methylpropylene, 1,1-dimethylethylene, 2,2-dimethylethylene, n-pentylene, n-hexylene, n-heptylene, n-octylene, n-decylene and n-pentadecanylene. The $C_{1-15}$ alkylene group is preferably a $C_{1-10}$ alkylene group, more preferably a $C_{1-6}$ alkylene group or a $C_{1-4}$ alkylene group, and even more preferably a $C_{1-2}$ alkylene group.

An example of the $C_{2-15}$ alkenylene group includes ethenylene (vinylene), 1-propenylene, 2-propenylene (allylene), butenylene, hexenylene, octenylene, decenylene and pentadecenylene. The $C_{2-15}$ alkenylene group is preferably a $C_{2-10}$ alkenylene group, more preferably a $C_{2-6}$ alkenylene group or a $C_{2-4}$ alkenylene group, and even more preferably ethenylene (vinylene) or 2-propenylene (allylene).

An example of the $C_{2-15}$ alkynylene group includes ethynylene, propynylene, butynylene, hexynylene, octynylene and pentadecynylene. The $C_{2-15}$ alkynylene group is preferably a $C_{2-10}$ alkynylene group, and more preferably a $C_{2-6}$ alkynylene group or a $C_{2-4}$ alkynylene group.

The "$C_{3-15}$ cyclic aliphatic hydrocarbon group" means a cyclic saturated aliphatic hydrocarbon group having a carbon number of 1 or more and 15 or less. An example of a $C_{3-15}$ divalent cyclic aliphatic hydrocarbon group includes a $C_{3-15}$ cyclic alkylene group, a $C_{4-15}$ cyclic alkenylene group and a $C_{4-15}$ cyclic alkynylene group, and preferably $C_{3-10}$ cyclic alkylene group, a $C_{4-10}$ cyclic alkenylene group and a $C_{4-10}$ cyclic alkynylene group.

The "$C_{6-15}$ aromatic hydrocarbon group" is an aromatic hydrocarbon group having a carbon number of 6 or more and 15 or less. An example of a $C_{6-15}$ divalent aromatic hydrocarbon group includes phenylene, indenylene, naphthylene, biphenylene, phenalenylene, phenanthrenylene and anthracenylene, and is preferably a $C_{6-12}$ divalent aromatic hydrocarbon group and more preferably phenylene.

For example, the alkylene group means a divalent saturated aliphatic hydrocarbon group in the above definitions of the groups. When the "n" in the amine compound $R^1$—$(NH_2)_n$ is 1, the alkylene group is replaced with a monovalent alkyl group, and when the "n" is 3, the alkylene group is replaced with a trivalent alkylidyne group. For example, when the "n" is 1, divalent ethylene (—$CH_2CH_2$—) is replaced with methyl (—$CH_2CH_3$), and when the "n" is 3, divalent ethylene is replaced with ethylidyne (—$CH_2CH$<).

The above organic group may have a substituent other than a nucleophilic group, which is reacted with an isocyanate group. An example of a substituent of a $C_{1-15}$ chain aliphatic hydrocarbon includes one or more substituents selected from a $C_{1-6}$ alkoxy group, a $C_{1-7}$ acyl group, a halogeno group, a nitro group, a cyano group, a carbamoyl group and —$SiR^{30}R^{31}R^{32}$. An example of a substituent of a $C_{3-15}$ cyclic aliphatic hydrocarbon group and a $C_{6-15}$ aromatic hydrocarbon group includes one or more substituents selected from a $C_{1-6}$ alkyl group, a $C_{1-6}$ alkoxy group, a $C_{1-7}$ acyl group, a halogeno group, a nitro group, a cyano group, a carbamoyl group and —$SiR^{30}R^{31}R^{32}$. An example of the "halogeno group" includes fluoro, chloro, bromo and iodo. The $R^{30}$ to $R^{32}$ are independently a $C_{1-6}$ alkyl group, a $C_{1-6}$ alkoxy group, vinyl, 2-(3,4-epoxycyclohexyl)ethyl, 3-glycidoxypropyl, p-styryl, 3-methacryloxypropyl, 3-acryloxypropyl, N-2-(aminoethyl)-3-aminopropylmethyl, 3-aminopropyl, N-(1,3-dimethyl-butylidene)propyl, N-phenyl-3-aminopropyl, N-(vinylbenzyl)-2-aminoethyl-3-aminopropyl, 3-ureidepropyl, 3-mercaptopropyl or 3-isocyanatepropyl, and at least one of $R^{30}$ to $R^{32}$ is a $C_{1-6}$ alkoxy group.

An example of the $R^1$ in the primary amine compound (I) in the case of n=2 includes the following group (II):

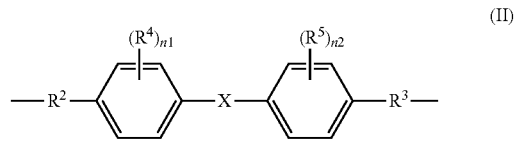

wherein $R^2$ and $R^3$ are independently —$(CR^6R^7)_{n1}$— or —(—O—$(CR^6R^7)_{n2}$—$)_{n3}$— (wherein $R^6$ and $R^7$ are independently H or a $C_{1-6}$ alkyl group, n1 is an integer of 0 or more and 10 or less, n2 is an integer of 1 or more and 10 or less, n3 is an integer of 1 or more and 10 or less, and when n1 or n2 is an integer of 2 or more, a plurality of $R^6$ or $R^7$ are the same as or different from each other), $R^4$ and $R^5$ are independently a halogeno group, a $C_{1-20}$ aliphatic hydrocarbon group, a $C_{1-20}$ alkoxy group, a $C_{3-20}$ cycloalkyl group, a $C_{6-20}$ aromatic hydrocarbon group, a $C_{7-20}$ aralkyl group, a $C_{6-20}$ aromatic hydrocarbon oxy group or a $C_{3-20}$ cycloalkoxy group, X is any one of the following groups:

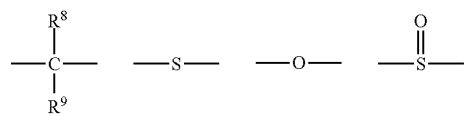

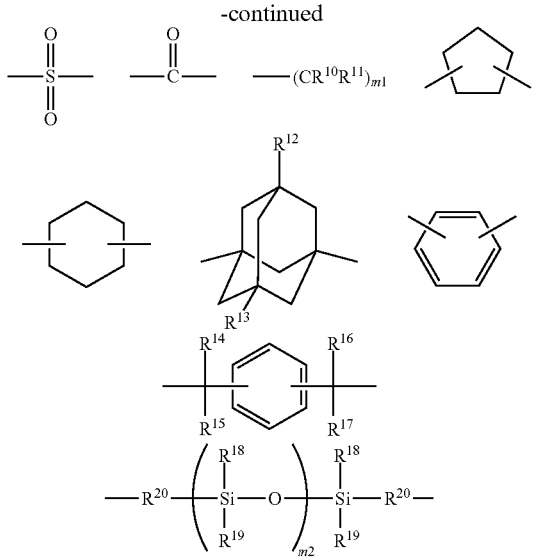

(wherein
$R^8$ and $R^9$ are independently H, a halogeno group, a $C_{1-20}$ aliphatic hydrocarbon group optionally having a substituent α, a $C_{1-20}$ alkoxy group optionally having a substituent α, a $C_{6-20}$ aromatic hydrocarbon group optionally having a substituent β, or $R^8$ and $R^9$ may bind together to form a $C_{3-20}$ carbon ring or a 5-12 membered hetero ring, $R^{10}$ and $R^{11}$ are independently H or a $C_{1-6}$ alkyl group, and when m1 is integer of 2 or more, a plurality of $R^{10}$ or $R^{11}$ may be the same as or different from each other, $R^{12}$ to $R^{19}$ are independently a halogeno group, a $C_{1-20}$ aliphatic hydrocarbon group optionally having a substituent α, a $C_{1-20}$ alkoxy group optionally having a substituent α, or a $C_6$-12 aromatic hydrocarbon group optionally having a substituent β, $R^{20}$ is a $C_{1-9}$ alkylene group optionally having a substituent α, m1 is an integer of 1 or more and 20 or less,
m2 is an integer of 1 or more and 500 or less.)
n1 and n2 are independently integers of 0 or more and 4 or less, substituent α is one or more substituents selected from a $C_{1-6}$ alkoxy group, a $C_{1-7}$ acyl group, a halogeno group, a nitro group, a cyano group, a carbamoyl group and —$SiR^{30}R^{31}R^{32}$, substituent β is one or more substituents selected from a $C_{1-6}$ alkyl group, a $C_{1-6}$ alkoxy group, a $C_{1-7}$ acyl group, a halogeno group, a nitro group, a cyano group, a carbamoyl group and —$SiR^{30}R^{31}R^{32}$.

An additive amount of the primary amine compound may be appropriately adjusted and may be adjusted to 0.5 mmol/mL or more and 100 mmol/mL or less to an initial amount of the halogenated methane. When the ratio is 0.5 mmol/mL or more, the reaction may proceed more efficiently, and when the ratio is 100 mmol/mL or less, the amine compound may be less likely to react with the generated isocyanate to generate a urea compound.

An irradiation of the high energy light may be stopped after the amine compound is added, and an irradiation of the high energy light is preferably stopped before the amine compound is added, since the isocyanate compound generated by the reaction may be possibly decomposed due to the irradiation of the high energy light.

A temperature for the reaction with the primary amine compound may be similarly adjusted to a temperature for the reaction to decompose the halogenated methane. In other words, the temperature may be adjusted to 15° C. or lower, and is preferably 10° C. or lower, more preferably 5° C. or lower and even more preferably 2° C. or lower. The lower limit of the temperature is not particularly restricted, and the temperature is preferably −80° C. or higher and more preferably −20° C. or higher or −15° C. or higher. When the reaction step is carried out at relatively low, a leakage of the halogenated carbonyl or halogenated carbonyl-like compound and a reaction and decomposition of the generated isocyanate compound can be suppressed more surely.

A base is preferably added in addition to the amine compound in this reaction step. Though a reactivity of the amine compound may be decreased due to a hydrogen halide as a side product, the reactivity of the amine compound can be maintained by a base. Such a base is not particularly restricted and is preferably one or more bases selected from a heterocyclic aromatic amine and a non-nucleophilic strong base, since a base having —$NH_2$ may possibly react with the generated isocyanate compound.

The heterocyclic aromatic amine means a compound that has at least one hetero ring and that has at least one of amine functional group other than —$NH_2$. An example of the heterocyclic aromatic amine includes pyridine and a derivative thereof, such as pyridine, α-picoline, β-picoline, γ-picoline, 2,3-lutidine, 2,4-lutidine, 2,6-lutidine, 3,5-lutidine, 2-chloropyridine, 3-chloropyridine, 4-chloropyridine, 2,4,6-trimethylpyridine and 4-dimethylaminopyridine.

The "non-nucleophilic strong base" means a strong base of which nucleophilicity of the lone electron pair on the nitrogen atom is weak due to steric hindrance. An example of the non-nucleophilic strong base includes triethylamine, N,N-diisopropylethylamine, tripropylamine, triisopropylamine, tributylamine, tripentylamine, trihexylamine, triheptylamine, trioctylamine, tridecylamine, tridodecylamine, triphenylamine, tribenzylamine, N,N-diisopropylethylamine, 1,5,7-triazabicyclo[4.4.0]dec-5-ene (TBD), 7-methyl-1,5,7-triazabicyclo[4.4.0]dec-5-ene (MTBD), 1,8-diazabicyclo[5.4.0]undec-7-ene (DBU), 1,5-diazabicyclo[4.3.0]non-5-ene (DBN) and 1,1,3,3-tetramethylguanidine (TMG). In addition, a base having relatively high basicity may be used. For example, a base of which basicity ($pK_{BH+}$) in acetonitrile is 20 or more, such as TBD ($pK_{BH+}$: 25.98), MTBD ($pK_{BH+}$: 25.44), DBU ($pK_{BH+}$: 24.33), DBN ($pK_{BH+}$: 23.89) and TMG ($pK_{BH+}$: 23.30), may be used.

In addition, a versatile organic amine such as trimethylamine, dimethylethylamine, diethylmethylamine, N-ethyl-N-methylbutylamine and 1-methylpyrrolidine can be used.

A usage amount of the base may be appropriately adjusted in the range that the reaction successfully proceeds and may be adjusted to 1 time or more by mole and 20 times or less by mole to 1 mole of the amine compound. The ratio is preferably 10 times or less by mole.

A reaction time is not particularly restricted and may be determined by a preliminary experiment, and the reaction may be sustained until the amine compound as the raw material compound is consumed. For example, the reaction time may be adjusted to 30 minutes or more and 10 hours or less.

When the base is not used and when the reaction is not completely completed even with using the base, the reaction temperature may be raised. For example, the reaction temperature may be adjusted to 20° C. or higher and 80° C. or lower. The reaction mixture may be heated to reflux for the reaction.

The isocyanate compound may be purified by a conventionally known method. An example of the purification method includes distillation, removal of the raw material compound under reduced pressure and column chromatography.

3. Application of Isocyanate Compound (1) Production of Carbamate

The isocyanate compound produced by the production method of the present invention can be used as a synthetic intermediate compound for a carbamate and a polyurethane. For example, a carbamate can be obtained by reacting the isocyanate compound with a monovalent alcohol. A reaction formula in the case where the isocyanate compound is a compound represented by $R^1$—(N=C=O), and a monovalent alcohol is a compound represented by $R^{21}$—OH is shown as follows.

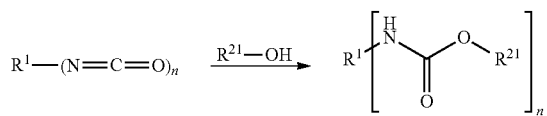

An example of the $R^{21}$ includes a hydrocarbon group, a monocyclic heteroaryl group and a polycyclic heteroaryl group. An example of the hydrocarbon group includes a $C_{1-30}$ alkyl group, a $C_{2-30}$ alkenyl group, a $C_{2-30}$ alkynyl group, a $C_{6-32}$ aromatic hydrocarbon group and a group formed by connecting 2 or more and 5 or less of the groups. The above groups may have a group other than a nucleophilic group that reacts with an isocyanate group. An example of the substituent that the hydrocarbon group may have includes one or more substituents selected from a $C_{1-6}$ alkoxy group, a $C_{1-7}$ acyl group, a halogeno group, a nitro group, a cyano group, a carbamoyl group and —$SiR^{30}R^{31}R^{32}$. An example of the substituent that the monocyclic heteroaryl group and the polycyclic heteroaryl group may have includes one or more substituents selected from a $C_{1-6}$ alkyl group, a $C_{1-6}$ alkoxy group, a $C_{1-7}$ acyl group, a halogeno group, a nitro group, a cyano group, a carbamoyl group and —$SiR^{30}R^{31}R^{32}$.

(2) Production of Polyurethane

A polyurethane can be produced by reacting a polyisocyanate compound that is produced by the production method of the present invention and that has 2 or more isocyanate groups with a polyol compound. In other words, the present invention also relates a method for producing a polyurethane, the method comprising the steps of producing a polyisocyanate compound having 2 or more isocyanate groups by the above-described method and adding a polyol compound to a reaction mixture of the above step comprising the polyisocyanate compound. For example, a polyurethane can be produced by reacting a polyisocyanate compound having two isocyanate groups with a polyol compound having 2 hydroxy groups as the following formula.

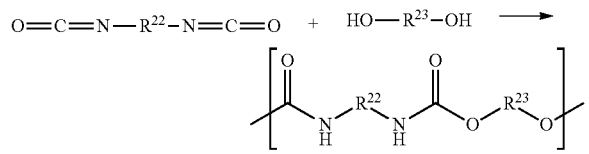

wherein $R^{22}$ is a divalent group in $R^1$, and an example of $R^{23}$ includes a divalent hydrocarbon group, a divalent monocyclic heteroaryl group and a divalent polycyclic heteroaryl group. An example of the divalent hydrocarbon group includes a $C_{1-30}$ alkylene group, a $C_{2-30}$ alkenylene group, a $C_{2-30}$ alkynylene group, a divalent $C_{6-32}$ aromatic hydrocarbon group and a group formed by connecting 2 or more and 5 or less of the groups. A part of the hydrogen atom of the above groups may be substituted by one or more substituents selected from a $C_{1-6}$ alkyl group, a $C_{1-6}$ alkoxy group, a $C_{1-7}$ acyl group, a halogeno group, a nitro group, a cyano group, carbamoyl group and —$SiR^{30}R^{31}R^{32}$.

The alcohol compound "$R^{24}$—(OH)$_p$" to be reacted with the isocyanate compound is not particularly restricted as long as the alcohol compound has p-pieces of hydroxy groups. An example of $R^{24}$ includes a p-valent hydrocarbon group, a p-valent monocyclic heteroaryl group and a p-valent polycyclic heteroaryl group. The alcohol compound may be linear or branched and may have a cyclic structure and an ether group, "—O—". The "p" may be, for example, 1 or more and 1,000 or less. The "p" is preferably 1 or more and 50 or less, preferably 20 or less or 10 or less, more preferably 5 or less or 3 or less, and particularly preferably 2.

As the polyol compound, the following polyether diol, polyester diol and polycarbonate diol may be used. In addition, an acrylic polyol may be used as the polyol compound.

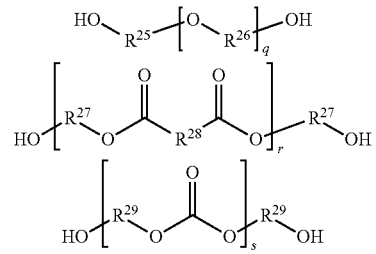

wherein $R^{25}$ to $R^{29}$ are independently a $C_{1-30}$ alkylene group optionally substituted by one or more substituents selected from a $C_{1-6}$ alkoxy group, a $C_{1-7}$ acyl group, a halogeno group, a nitro group, a cyano group, a carbamoyl group and —$SiR^{30}R^{31}R^{32}$, and q, r and s are independently integers of 1 or more and 50 or less.

The acrylic polyol is a polymer that is prepared by copolymerizing a (meth)acrylate alkyl ester, a hydroxy group-containing monomer and other monomer if needed and that has 2 or more hydroxy groups. The (meth)acrylate alkyl ester is not particularly restricted and is exemplified by a (meth)acrylate $C_{1-30}$ alkyl ester such as ethyl (meth)acrylate. An example of the hydroxy group-containing monomer includes a (meth)acrylate hydroxyalkyl ester such as 2-hydroxyethyl (meth)acrylate, 2-hydroxypropyl (meth)acrylate, 3-hydroxypropyl (meth)acrylate, 2-hydroxybutyl (meth)acrylate and 4-hydroxybutyl (meth)acrylate.

The "$C_{1-30}$ alkyl group" means a linear, branched or cyclic saturated aliphatic hydrocarbon group having a carbon number of 1 or more and 30 or less, and is exemplified by methyl, ethyl, n-propyl, isopropyl, cyclopropyl, n-butyl, isobutyl, s-butyl, t-butyl, cyclobutyl, n-pentyl, cyclopentyl, n-hexyl, cyclohexyl, heptyl, cycloheptyl, octyl, cyclooctyl, n-nonyl, n-decyl, n-icosyl and n-triacontyl. The $C_{1-30}$ alkyl group is preferably a $C_{1-20}$ alkyl group or a $C_{1-10}$ alkyl group, more preferably a $C_{1-6}$ alkyl group or a $C_{1-4}$ alkyl group, and even more preferably a $C_{1-2}$ alkyl group or methyl.

The "$C_{2-30}$ alkenyl group" means a linear, branched or cyclic unsaturated aliphatic hydrocarbon group that has a carbon number of 2 or more and 30 or less and at least one carbon-carbon double bond, and is exemplified by ethenyl (vinyl), 1-propenyl, 2-propenyl (allyl), isopropenyl, 2-butenyl, 3-butenyl, isobutenyl, pentenyl, hexenyl, octenyl, decenyl, icosenyl and triacontenyl. The $C_{2-30}$ alkenyl group is preferably a $C_{2-20}$ alkenyl group or a $C_{2-10}$ alkenyl group, more preferably a $C_{2-6}$ alkenyl group or a $C_{2-4}$ alkenyl group, and even more preferably ethenyl (vinyl) or 2-propenyl (allyl).

The "$C_{2-30}$ alkynyl group" means a linear, branched or cyclic unsaturated aliphatic hydrocarbon group that has a carbon number of 2 or more and 30 or less and at least one carbon-carbon triple bond, and is exemplified by ethynyl, 1-propynyl, 2-propynyl, 2-butynyl, 3-butynyl, pentynyl, hexynyl, octynyl, decynyl, icosynyl and triacontynyl. The $C_{2-30}$ alkynyl group is preferably a $C_{2-20}$ alkynyl group or a $C_{2-10}$ alkynyl group, more preferably a $C_{2-6}$ alkynyl group or a $C_{2-4}$ alkynyl group.

The "$C_{6-32}$ aromatic hydrocarbon group" is an aromatic hydrocarbon group having a carbon number of 6 or more and 32 or less, and is exemplified by phenyl, indenyl, naphthyl, biphenyl, phenalenyl, phenanthrenyl, anthracenyl, triphenylenyl, pyrenyl, naphthacenyl, perylenyl, pentacenyl, hexacenyl, coronenyl, trinaphthylenyl, heptacenyl and ovalenyl. The $C_{6-32}$ aromatic hydrocarbon group is preferably a $C_{6-20}$ aromatic hydrocarbon group, more preferably a $C_{6-12}$ aromatic hydrocarbon group and even more preferably phenyl.

The "monocyclic heteroaryl group" means a 5-membered monocyclic aromatic heterocyclic group or a 6-membered monocyclic aromatic heterocyclic group that has at least one of a hetero atom such as a nitrogen atom, an oxygen atom or a sulfur atom but does not have a nucleophilic group >NH. An example of the monocyclic heteroaryl group includes a 5-membered monocyclic heteroaryl group such as thienyl, furyl, oxazolyl, isooxazolyl, thiazolyl, isothiazolyl and thiadiazole; and a 6-membered monocyclic heteroaryl group such as pyridinyl, pyrazinyl, pyrimidinyl and pyridazinyl.

The "polycyclic heteroaryl group" means a polycyclic aromatic heterocyclic group that has at least one of a hetero atom such as a nitrogen atom, an oxygen atom or a sulfur atom, and is formed by connecting through a single bond or condensing the above-described monocyclic heteroaryl groups or the above-described monocyclic heteroaryl group and aromatic hydrocarbon group. An example of the polycyclic heteroaryl group includes indolyl, isoindolyl, quinolinyl, isoquinolinyl, benzofuranyl, isobenzofuranyl and chromenyl.

The above organic group may have a substituent other than a reactive group that is reacted with the generated isocyanate compound. An example of the substituent includes one or more substituents selected from a $C_{1-6}$ alkyl group, a $C_{1-6}$ alkoxy group, a $C_{1-7}$ acyl group, a halogeno group, a nitro group, a cyano group, a carbamoyl group and —$SiR^{30}R^{31}R^{32}$.

When the "p" in the alcohol compound $R^{24}$—$(OH)_p$ is an integer of 2 or more and $R^{24}$ is a 2 or more-valent organic group, the above-described specific examples of the monovalent organic group may be read as an n-valent organic group wherein n is 2 or more. For example, "n" is 2, the above described $C_{1-30}$ alkyl group may be read as a $C_{1-30}$ alkylene group, and when "n" is 3, the above-described $C_{1-30}$ alkyl group may be read as a $C_{1-30}$ alkylidyne group.

The $C_{1-30}$ alkyl group, $C_{2-30}$ alkenyl group, $C_{2-30}$ alkynyl group and $C_{6-32}$ aromatic hydrocarbon group may have 1 or more substituents selected from a $C_{1-6}$ alkoxy group, a halogeno group, a nitro group and a cyano group. An example of the halogeno group includes 1 or more halogeno groups selected from fluoro, chloro, bromo and iodo.

An example of a fluoro alcohol having one hydroxy group includes monofluoroethanol, difluoroethanol, trifluoroethanol, monofluoropropanol, difluoropropanol, trifluoropropanol, tetrafluoropropanol, pentafluoropropanol, hexafluoropropanol, monofluorobutanol, difluorobutanol, trifluorobutanol, tetrafluorobutanol, pentafluorobutanol, hexafluorobutanol, heptafluorobutanol, monofluoropentanol, difluoropentanol, trifluoropentanol, tetrafluoropentanol, pentafluoropentanol, hexafluoropentanol, heptafluoropentanol, octafluoropentanol, nonafluoropentanol, monofluorohexanol, difluorohexanol, trifluorohexanol, tetrafluorohexanol, pentafluorohexanol, hexafluorohexanol, heptafluorohexanol, octafluorohexanol, nonafluorohexanol, decafluorohexanol, undecafluorohexanol, monofluoroheptanol, difluoroheptanol, trifluoroheptanol, tetrafluoroheptanol, pentafluoroheptanol, hexafluoroheptanol, heptafluoroheptanol, octafluoroheptanol, nonafluoroheptanol, decafluoroheptanol, undecafluoroheptanol, dodecafluoroheptanol, tridecafluoroheptanol, monofluorooctanol, difluorooctanol, trifluorooctanol, tetrafluorooctanol, pentafluorooctanol, hexafluorooctanol, heptafluorooctanol, octafluorooctanol, nonafluorooctanol, decafluorooctanol, undecafluorooctanol, dodecafluorooctanol, tridecafluorooctanol, tetradecafluorooctanol, pentadecafluorooctanol, monofluorononanol, difluorononanol, trifluorononanol, tetrafluorononanol, pentafluorononanol, hexafluorononanol, heptafluorononanol, octafluorononanol, nonafluorononanol, decafluorononanol, undecafluorononanol, dodecafluorononanol, tridecafluorononanol, tetradecafluorononanol, pentadecafluorononanol, hexadecafluorononanol, heptadecafluorononanol, monofluorodecanol, difluorodecanol, trifluorodecanol, tetrafluorodecanol, pentafluorodecanol, hexafluorodecanol, heptafluorodecanol, octafluorodecanol, nonafluorodecanol, decafluorodecanol, undecafluorodecanol, dodecafluorodecanol, tridecafluorodecanol, tetradecafluorodecanol, pentadecafluorodecanol, hexadecafluorodecanol, heptadecafluorodecanol, octadecafluorodecanol and nonadecafluorodecanol.

An example of a fluoro alcohol having an aromatic hydrocarbon group and one hydroxy group includes monofluorophenol, difluorophenol, trifluorophenol, tetrafluorophenol, pentafluorophenol, trifluoromethylphenol, monofluorobenzyl alcohol, difluorobenzyl alcohol, trifluorobenzyl alcohol, tetrafluorobenzyl alcohol, pentafluorobenzyl alcohol, trifluoromethylbenzyl alcohol, monofluorophenoxyethanol, difluorophenoxyethanol, trifluorophenoxyethanol, tetrafluorophenoxyethanol and pentafluorophenoxyethanol.

An example of a fluoro alcohol having two hydroxy groups includes monofluoropropylene glycol, difluoropropylene glycol, monofluorobutanediol, difluorobutanediol, trifluorobutanediol, tetrafluorobutanediol, monofluoropentanediol, difluoropentanediol, trifluoropentanediol, tetrafluoropentanediol, pentafluoropentanediol, hexafluoropentanediol, monofluorohexanediol, difluorohexanediol, trifluorohexanediol, tetrafluorohexanediol, pentafluorohexanediol, hexafluorohexanediol, heptafluorohexanediol, octafluorohexanediol, monofluoroheptanediol, difluoroheptanediol, trifluoroheptanediol, tetrafluoroheptanediol, pentafluoroheptanediol, hexafluoroheptanediol, heptafluoroheptanediol, octafluoroheptanediol, nonafluoroheptanediol, decafluoroheptanediol, monofluorooctanediol, difluorooctanediol, trifluorooctanediol, tetrafluorooctanediol, pentafluorooctanediol, hexafluorooctanediol, heptafluorooctanediol, octafluorooctanediol, nonafluorooctanediol, decafluorooctanediol, undecafluorooctanediol, dodecafluorooctanediol, monofluorononanediol, difluorononanediol, trifluorononanediol, tetrafluorononanediol, pentafluorononanediol, hexafluorononanediol, heptafluorononanediol, octafluorononanediol, nonafluorononanediol, decafluorononanediol, undecafluorononanediol, dodecafluorononanediol, tridecafluorononanediol, tetradecafluorononanediol, monofluorodecanediol, difluorodecanediol, trifluorodecanediol, tetrafluorodecanediol, pentafluorodecanediol, hexafluorodecanediol, heptafluorodecanediol, octafluorodecanediol, nonafluorodecanediol, decafluorodecanediol, undecafluorodecanediol, dodecafluorodecanediol, tridecafluorodecanediol, tetradecafluorodecanediol, pentadecafluorodecanediol and hexadecafluorodecanediol.

An example of an alcohol having an aromatic hydrocarbon and two hydroxy groups includes monofluorobenzenediol, difluorobenzenediol, trifluorobenzenediol, tetrafluorobenzenediol, monofluorobenzenedimethanol, difluorobenzenedimethanol, trifluorobenzenedimethanol, tetrafluorobenzenedimethanol and 2,2-bis(4-hydroxyphenyl)hexafluoropropane.

An example of a fluoro alcohol having three hydroxy groups includes monofluoropentanetriol, difluoropentanetriol, monofluorohexanetriol, difluorohexanetriol, trifluorohexanetriol, tetrafluorohexanetriol, monofluoroheptanetriol, difluoroheptanetriol, trifluoroheptanetriol, tetrafluoroheptanetriol, pentafluoroheptanetriol, hexafluoroheptanetriol, monofluorooctanetriol, difluorooctanetriol, trifluorooctanetriol, tetrafluorooctanetriol, pentafluorooctanetriol, hexafluorooctanetriol, heptafluorooctanetriol, octafluorooctanetriol, monofluorononanetriol, difluorononanetriol, trifluorononanetriol, tetrafluorononanetriol, pentafluorononanetriol, hexafluorononanetriol, heptafluorononanetriol, octafluorononanetriol, nonafluorononanetriol, decafluorononanetriol, monofluorodecanetriol, difluorodecanetriol, trifluorodecanetriol, tetrafluorodecanetriol, pentafluorodecanetriol, hexafluorodecanetriol, heptafluorodecanetriol, octafluorodecanetriol, nonafluorodecanetriol, decafluorodecanetriol, undecafluorodecanetriol and dodecafluorodecanetriol.

An example of a fluoro alcohol having four or more hydroxy groups includes nonafluorohexanetetraol, decafluorohexanetetraol, monofluoroheptanetetraol, difluoroheptanetetraol, monofluorooctanetetraol, difluorooctanetetraol, trifluorooctanetetraol, tetrafluorooctanetetraol, monofluorononanetetraol, difluorononanetetraol, trifluorononanetetraol, tetrafluorononanetetraol, pentafluorononanetetraol, hexafluorononanetetraol, monofluorodecanetetraol, difluorodecanetetraol, trifluorodecanetetraol, tetrafluorodecanetetraol, pentafluorodecanetetraol, hexafluorodecanetetraol, heptafluorodecanetetraol and octafluorodecanetetraol.

(3) Reaction Conditions

An additive amount of the alcohol compound to be reacted with the isocyanate compound may be appropriately adjusted, and for example, the same mole or nearly the same mole of the alcohol compound as the used primary amine compound may be used. The term "nearly the same mole" in this disclosure means 0.8 times or more by mole and 1.2 times or less by mole and preferably 0.9 times or more by mole and 1.1 times or less by mole. The carbamate and polyurethane can be produced in the same reaction system by adding the alcohol compound to the reaction mixture for the above-described method for producing an isocyanate compound according to the present invention.

A reaction time is not particularly restricted and may be determined by a preliminary experiment, and the reaction may be sustained until the isocyanate compound or the alcohol compound is consumed. For example, the reaction time may be adjusted to 30 minutes or more and 50 hours or less. A reaction temperature may be adjusted similarly to the reaction temperature for the primary amine compound and may be adjusted to 20° C. or higher and 80° C. or lower to accelerate the reaction.

The carbamate and polyurethane may be purified by a conventionally known method. An example of such a purification method includes distillation, chromatography, washing using a poor solvent, and recrystallization.

The present application claims the benefit of the priority date of Japanese patent application No. 2018-214988 filed on Nov. 15, 2018. All of the contents of the Japanese patent application No. 2018-214988 filed on Nov. 15, 2018, are incorporated by reference herein.

EXAMPLES

Hereinafter, the examples are described to demonstrate the present invention more specifically, but the present invention is in no way restricted by the examples, and the examples can be appropriately modified to be carried out within a range that adapts to the contents of this specification. Such a modified example is also included in the range of the present invention.

Example 1: Synthesis of Phenylisocyanate

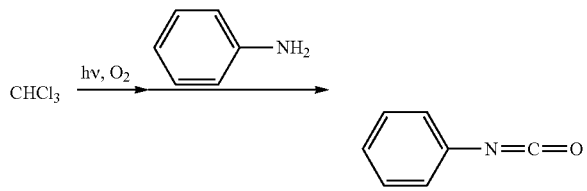

A quartz glass jacket having a diameter of 30 mm was inserted into a cylindrical reaction vessel having a diameter of 42 mm and a volume of 100 mL, and a low pressure mercury lamp ("UVL20PH-6" manufactured by SEN Light, 20 W, (φ24×120 mm) was further inserted into the quartz glass jacket to construct a reaction system. A schematic picture of the reaction system is shown in the figure. The light irradiated from the low pressure mercury lamp contained UV-C having a wavelength of 254 nm, and the illumination intensity of the light having a wavelength of 254 nm at the position 5 mm from the tube wall was 6.23 to 9.07 mW/cm$^2$. Purified chloroform (50 mL) was added into the reaction vessel. Oxygen gas was blown into the stirred chloroform at a flow rate of 0.5 L/min at 0° C. to cause bubbling, and a light containing UV-C was irradiated from the low pressure mercury lamp.

The power of the low pressure mercury lamp was turned off after 3 hours, and a chloroform solution (5 mL) of aniline (0.91 mL, 10 mmol) was added under illumination of a general room lamp. The mixture was stirred at 0° C. for 10 minutes. Then, 2,6-lutidine (5.81 mL, 50 mmol) was added, and the mixture was stirred at 0° C. for 1 hour.

The reaction mixture was analyzed by $^1$H NMR; as a result, it was confirmed that phenylisocyanate as the target compound was produced with the yield of 97%.

Example 2: Synthesis of Phenylisocyanate

The reaction was carried out similarly to Example 1 except that 2,6-lutidine (5.81 mL, 50 mmol) was changed to pyridine (4 mL, 50 mmol).

The reaction mixture was analyzed by $^1$H NMR; as a result, it was confirmed that phenylisocyanate as the target compound was produced with the yield of >99%.

Example 3: Synthesis of Phenylisocyanate

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of aniline (0.91 mL, 10 mmol) was added under illumination of a general room lamp. The mixture was stirred at 0° C. for 10 minutes. Then, the temperature was elevated to 60° C. and the mixture was stirred for 1.5 hours.

The reaction mixture was analyzed by $^1$H NMR; as a result, it was confirmed that phenylisocyanate as the target compound was produced with the yield of 80%.

Example 4: Synthesis of Hexylisocyanate

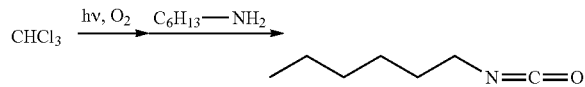

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of hexylamine (1.33 mL, 10 mmol) was added under illumination of a general room lamp. The mixture was stirred at 0° C. for 10 minutes. Then, pyridine (4 mL, 50 mmol) was added, and the mixture was stirred at 0° C. for 1 hour.

The reaction mixture was analyzed by 1H NMR; as a result, it was confirmed that hexylisocyanate as the target compound was produced with the yield of >99%.

Example 5: Synthesis of Hexamethylenediisocyanate

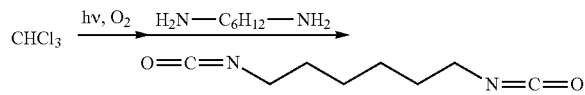

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (10 mL) of hexamethylenediamine (0.58 g, 5 mmol) was added under illumination of a general room lamp. The mixture was stirred at 0° C. for 10 minutes. Then, pyridine (4 mL, 50 mmol) was added, and the mixture was stirred at 0° C. for 1 hour and further at 60° C. for 1.5 hours.

The yellow cloudy reaction mixture was filtered and the filtrate was analyzed by $^1$H NMR; as a result, it was confirmed that hexamethylenediisocyanate as the target compound was produced with the yield of 96%. The solvent was distilled away under reduced pressure from the reaction mixture, n-hexane (50 mL) was added, and the mixture was stirred at room temperature under argon atmosphere. The generated precipitate was separated by filtration, and the solvent was distilled away from the filtrate. The obtained oily product was subjected to distillation under reduced pressure using a glass tube oven, and the fraction (0.6 g) of 100° C. at 0.2 kPa was isolated. The obtained colorless liquid was analyzed by $^1$H NMR and FT-IR spectra; as a result, it was confirmed that hexamethylenediisocyanate as the target compound was produced with the yield of 71%.

Example 6: Synthesis of 2,2-difluoroethylisocyanate

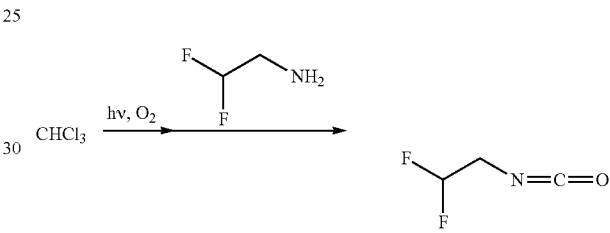

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of 2,2-difluoroethylamine (0.7 mL, 10 mmol) was added under illumination of a general room lamp. The mixture was stirred at 0° C. for 10 minutes. Then, pyridine (4 mL, 50 mmol) was added, and the mixture was stirred at 0° C. for 1 hour. Dichloromethane (320 µL) as an internal standard was added to the reaction mixture and the mixture was analyzed by 1H NMR; as a result, it was confirmed that 2,2-difluoroethylisocyanate as the target compound was produced with the yield of 66%.

Example 7: Synthesis of Toluene-2,4-Diisocyanate

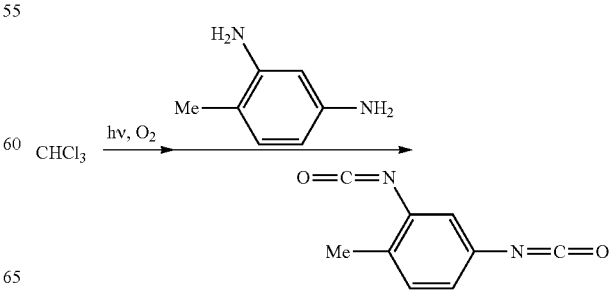

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (10 mL) of 2,4-diaminotoluene (0.61 g, 5 mmol) was added under illumination of a general room lamp. The mixture was stirred at −20° C. for 10 minutes. Then, pyridine (4 mL, 50 mmol) was added, and the mixture was stirred at −20° C. for 1 hour.

Dichloromethane (480 μL) as an internal standard was added to the reaction mixture and the mixture was analyzed by 1H NMR; as a result, it was confirmed that toluene-2,4-diisocyanate as the target compound was produced with the yield of 80%.

Example 8: Synthesis of 4-fluorophenylisocyanate

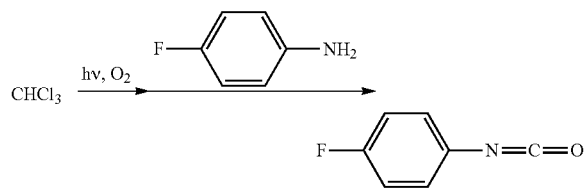

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of 4-fluoroaniline (0.96 mL, 10 mmol) was added under illumination of a general room lamp. The mixture was stirred at 0° C. for 10 minutes. Then, pyridine (4 mL, 50 mmol) was added, and the mixture was stirred at 0° C. for 1 hour.

Dichloromethane (640 μL) as an internal standard was added to the reaction mixture and the mixture was analyzed by 1H NMR; as a result, it was confirmed that 4-fluorophenylisocyanate as the target compound was produced with the yield of 62%.

Example 9: Synthesis of Methylenediphenyldiisocyanate

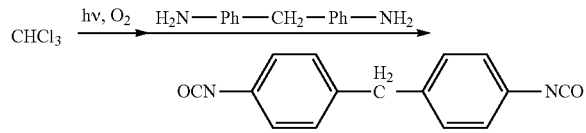

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of methylenediphenyldiamine (1.0 g, 5 mmol) was added under illumination of a general room lamp. The mixture was stirred at −30° C. for 10 minutes. Then, pyridine (4 mL, 50 mmol) was added, and the mixture was stirred at −30° C. for 1 hour.

Dichloromethane (320 μL) as an internal standard was added to the reaction mixture and the mixture was analyzed by $^1$H NMR; as a result, it was confirmed that methylenediphenyldiisocyanate as the target compound was produced with the yield of 90%.

Example 10: Synthesis of Carbamate

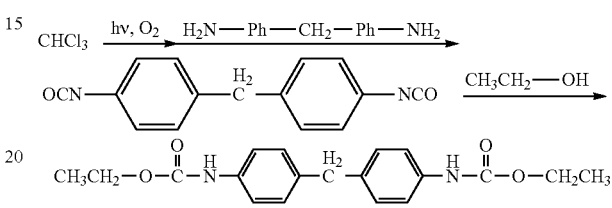

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of methylenediphenyldiamine (1.0 g, 5 mmol) was added under illumination of a general room lamp. The mixture was stirred at −30° C. for 10 minutes. Then, pyridine (4 mL, 50 mmol) was added, and the mixture was stirred at −30° C. for 1 hour.

Ethanol (0.6 mL, 10 mmol) was further added to the reaction mixture, and the mixture was stirred at room temperature for 12 hours.

Then, water and dichloromethane were added to the reaction mixture, and the organic phase and the aqueous phase were separated. The organic phase was dried over anhydrous sodium sulfate and then concentrated under reduced pressure. A recrystallization was carried out using dichloromethane and hexane, and the precipitated crystal was collected by filtration and dried in vacuo. The obtained light brown solid was analyzed by $^1$H NMR; as a result, it was confirmed that the carbamate as the target compound was produced with the yield of 81%.

Example 11: Synthesis of Polyurethane

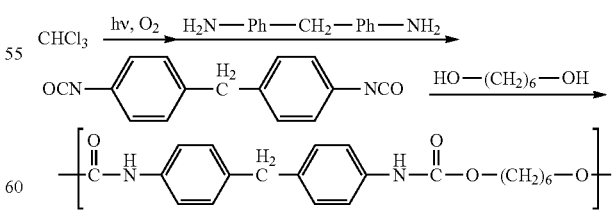

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of methylenediphenyldiamine (1.0 g, 5 mmol) was added under illumination of a general room lamp. The mixture was stirred at −20° C. for 10 minutes. Then, pyridine (4 mL, 50 mmol) was added, and the mixture was stirred at −20° C. for 1 hour.

A chloroform solution (5 mL) of 1,6-hexanediol (0.59 g, 5 mmol) was further added to the reaction mixture, and the mixture was stirred at room temperature for 12 hours.

Then, the reaction mixture was concentrated to some extent under reduced pressure, and then water and dichloromethane were added to the mixture, and the organic phase and the aqueous phase were separated. The organic phase was dried over anhydrous sodium sulfate and then concentrated under reduced pressure. Dichloromethane and hexane were added for reprecipitation, and the precipitated solid was collected by filtration and dried in vacuo.

In addition, a light brown solid was precipitated in the aqueous phase. The solid was collected by filtration and dried in vacuo.

The obtained two crystals were analyzed by $^1$H NMR. The peaks originated from polyurethane were found in both of the samples, and it was confirmed that the polyurethane obtained from the organic phase had a smaller molecular weight and the polyurethane obtained from the aqueous phase had a lager molecular weight. The combined amount and yield of the both crystals were 0.92 g and 50%, respectively.

The obtained polyurethane was analyzed by gel permeation chromatography (GPC) in the following conditions to measure the molecular weight. The result is shown in Table 1.

Apparatus: High speed GPC system composed of "Co-2060Plus", "MD-2018Plus", "PU-2089Plus" and "LC-NetII/ADC" manufactured by JASCO Corporation Column: "TSKgel G3000HHR" and "TSKgel G4000HHR" in series (respectively 4.6 mm×150 mm, manufactured by Tosoh)

Moving phase: THF Flow rate: 0.5 mL/min

Oven temperature: 20° C. Concentration: 0.2 w/v %

Injection amount: 5 µL Standard of molecular weight: polystyrene

Detector: PDA

TABLE 1

| Mw | Mn | Mw/Mn |
|---|---|---|
| 4,089 | 2,188 | 1.87 |

Example 12: Synthesis of Isophoronediisocyanate (IPDI)

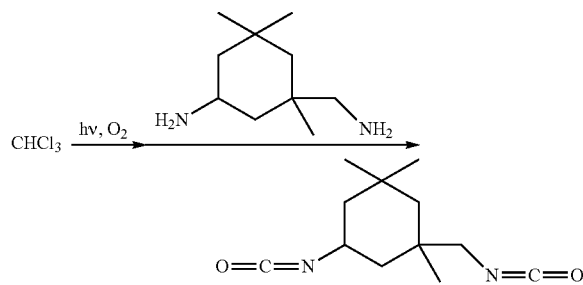

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of isophoronediamine (cis-trans mixture) (0.92 mL, 5 mmol) was added, and then pyridine (4 mL, 50 mmol) was added. The mixture was stirred at 0° C. for 30 minutes. To the reaction mixture, 1,2-dichloroethane (0.79 mL, 10 mmol) was added as an internal standard for the analysis by $^1$H NMR; as a result, it was confirmed that isophoronediisocyanate as the target compound was produced with the yield of 42%.

Example 13: Synthesis of m-xylylenediisocyanate (XDI)

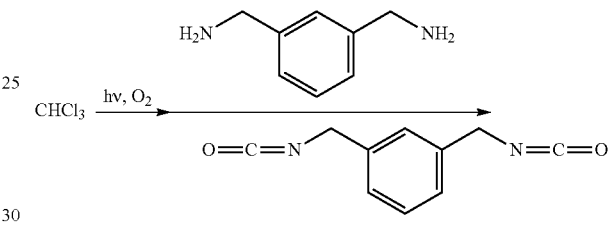

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of m-xylylenediamine (0.65 mL, 5 mmol) was added under illumination of a general room lamp. Then, pyridine (4 mL, 50 mmol) was added. The mixture was stirred at 0° C. for 30 minutes. To the reaction mixture, 1,2-dichloroethane (0.4 mL, 5 mmol) was added as an internal standard for the analysis by $^1$H NMR; as a result, it was confirmed that m-xylylenediisocyanate as the target compound was produced with the yield of 63%.

Example 14: Synthesis of Polyurethane from MDA and PPG

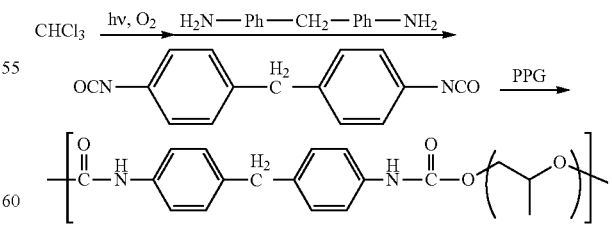

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of methylenediphenyldiamine (1.0 g, 5 mmol) was added under illumination of a general room lamp. The mixture was stirred at −20° C. for 10 minutes. Then, pyridine (4 mL, 50 mmol) was added, and the mixture was stirred at −20° C. for 1 hour. Dichloromethane (320 μL) was added to the reaction mixture as an internal standard for the analysis by ¹H NMR; as a result, it was confirmed that methylenediphenyldiisocyanate as the target compound was produced with the yield of 72%.

A mixture of 2 mL of pyridine and polypropylene glycol (average molecular weight: 400, 2 mL, 5 mmol) was further added to the reaction mixture, and the mixture was stirred at room temperature overnight.

Then, after the reaction mixture was stirred at 60° C. for 1 hour, and the reaction mixture was concentrated to some extent. Hydrochloric acid and dichloromethane was added, and the organic phase and the aqueous phase were separated. The organic phase was washed with brine, dried over anhydrous sodium sulfate, and concentrated under reduced pressure. The obtained oily compound was dried in vacuo. The amount and yield were 1.95 g and 83%, respectively.

The obtained polyurethane was analyzed by gel permeation chromatography (GPC) in the same conditions as Example 11 to measure the molecular weight. The result is shown in Table 2.

TABLE 2

| Mw | Mn | Mw/Mn |
|---|---|---|
| 2,113 | 1,363 | 1.55 |

Example 15: Synthesis of 2,2,3,3,4,4,5,5-octafluoro-1,6-diisocyanatohexane

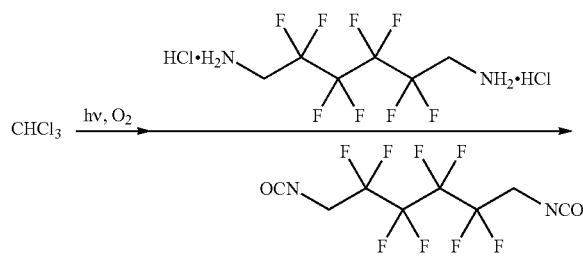

Purified chloroform (50 mL) and 2,2,3,3,4,4,5,5-octafluorohexane-1,6-diamine hydrochloride (1.0 g) were added into the reaction vessel of the reaction system used in Example 1, and oxygen gas was blown into the stirred mixture at a flow rate of 0.5 L/min at 0° C. to cause bubbling and a light containing UV-C was irradiated.

The power of the low pressure mercury lamp was turned off after 3 hours, and pyridine (4 mL, 50 mmol) was added under illumination of a general room lamp. The mixture was stirred at 0° C. for 1 hour. Dichloromethane (384 μL) was added to the reaction mixture as an internal standard for the analysis by ¹H NMR; as a result, it was confirmed that 2,2,3,3,4,4,5,5-octafluoro-1,6-diisocyanatohexane as the target compound was produced with the yield of 98%.

Example 16: Synthesis of bis(2-isocyanatoethyl)sulfane

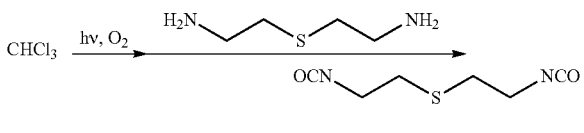

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of 2,2-thiobis(ethylamine) (1.15 mL, 10 mmol) was added under illumination of a general room lamp. Then, pyridine (4 mL, 50 mmol) was added, and the mixture was stirred at 0° C. for 30 minutes. Dichloromethane (1.28 mL) was added to the reaction mixture as an internal standard for the analysis by ¹H NMR; as a result, it was confirmed that bis(2-isocyanatoethyl)sulfane as the target compound was produced with the yield of 34%.

Example 17: Synthesis of (3-isocyanatopropyl)trimethoxysilane

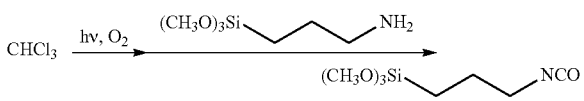

Purified chloroform (60 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of 3-aminopropyltrimethoxysilane (3.6 mL, 20 mmol) was added under illumination of a general room lamp. Then, lutidine (11.2 mL, 100 mmol) was added, and the mixture was stirred at 0° C. for 1 hour. To the reaction mixture, 1,2-dichloroethane (0.79 mL, 10 mmol) was added as an internal standard for the analysis by ¹H NMR; as a result, it was confirmed that (3-isocyanatopropyl)trimethoxysilane as the target compound was produced with the yield of 93%.

Example 18: Synthesis of (3-isocyanatopropyl)triethoxysilane

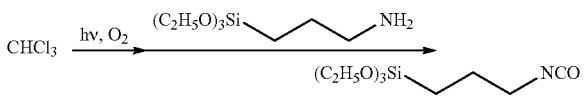

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of 3-aminopropyltriethoxysilane (2.4 mL, 10 mmol) was added under illumination of a general room lamp. Then, lutidine (5.8 mL, 50 mmol) was added, and the mixture was stirred at 0° C. for 1 hour. Dichloromethane (0.64 mL, 10 mmol) was added to the reaction mixture as an internal standard for the analysis by $^1$H NMR; as a result, it was confirmed that (3-isocyanatopropyl)triethoxysilane as the target compound was produced with the yield of 56%.

Example 19: Synthesis of Fluorine-Containing Biscarbamate

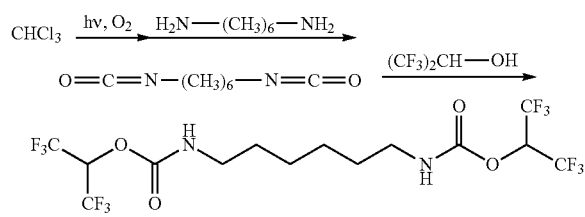

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (10 mL) of hexamethylenediamine (0.58 g, 5 mmol) was added and the mixture was stirred at 0° C. for 10 minutes under illumination of a general room lamp. Then, pyridine (4 mL, 50 mmol) was added, and the mixture was stirred at 0° C. for 30 minutes and further at 60° C. for 1.5 hours. Dichloromethane (0.64 mL, 10 mmol) was added to the reaction mixture as an internal standard for the analysis by $^1$H NMR; as a result, it was confirmed that hexamethylenediisocyanate as the target compound was produced with the yield of 96%.

Hexafluoro-2-propanol (5.3 mL, 50 mmol) was further added to the reaction mixture, and the mixture was stirred at room temperature for 3 days. Then, water and dichloromethane were added to the mixture, and the organic phase and the aqueous phase were separated. The organic phase was dried over anhydrous sodium sulfate and concentrated under reduced pressure. The obtained residue was subjected to silica-gel chromatography (eluent: THF) for purification and recrystallization using dichloromethane. The precipitated crystal was collected by filtration and dried in vacuo. The obtained white solid was analyzed by $^1$H NMR; as a result, it was confirmed that fluorine-containing biscarbamate[bis (1,1,1,3,3,3-hexafluoropropane-2-yl)hexane-1,6-diyldicarbamate] as the target compound was produced with the yield of 23%.

Example 20: Synthesis of 1,3-bis(isocyanatomethyl)cyclohexane

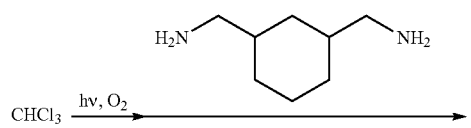

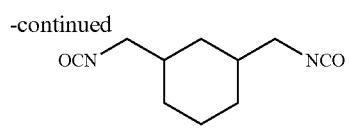

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of 1,3-bis(aminomethyl)cyclohexane (cis-trans mixture) (0.76 mL, 5 mmol) was added under illumination of a general room lamp. Then, pyridine (4 mL, 50 mmol) was added, and the mixture was stirred at 0° C. for 30 minutes. To the reaction mixture, 1,2-dichloroethane (395 μL, 5 mmol) was added as an internal standard for the analysis by $^1$H NMR; as a result, it was confirmed that 1,3-bis(isocyanatomethyl) cyclohexane as the target compound was produced with the yield of 58%.

Example 21: Synthesis of 1,5-naphthalenediisocyanate

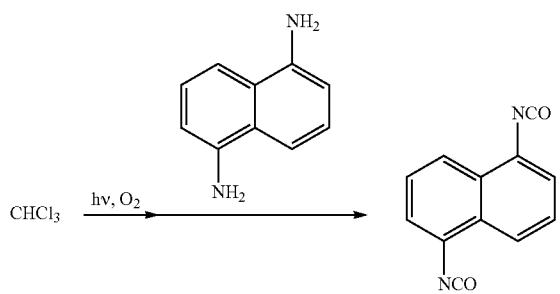

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of 1,5-diaminonaphthalene (0.79 g, 5 mmol) was added under illumination of a general room lamp. Then, pyridine (4 mL, 50 mmol) was added, and the mixture was stirred at 0° C. for 30 minutes. To the reaction mixture, 1,2-dichloroethane (198 μL, 2.5 mmol) was added as an internal standard for the analysis by $^1$H NMR; as a result, it was confirmed that 1,5-naphthalenediisocyanate as the target compound was produced with the yield of 67%.

Example 22: Synthesis of Norbornenediisocyanate

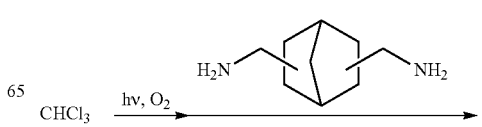

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of norbornenediamine (NBDA, 0.77 mL, 5 mmol) was added under illumination of a general room lamp. Then, pyridine (4 mL, 50 mmol) was added, and the mixture was stirred at 0° C. for 30 minutes. To the reaction mixture, 1,2-dichloroethane (395 µL, 5 mmol) was added as an internal standard for the analysis by $^1$H NMR; as a result, it was confirmed that norbornenediisocyanate as the target compound was produced with the yield of 65%.

Example 23: Synthesis of Pentamethylenediisocyanate

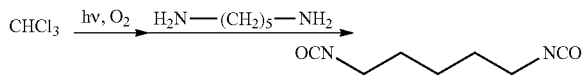

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of pentamethylenediamine (PDA) (0.59 mL, 5 mmol) was added under illumination of a general room lamp. Then, pyridine (4 mL, 50 mmol) was added, and the mixture was stirred at 0° C. for 30 minutes. To the reaction mixture, 1,2-dichloroethane (395 µL, 5 mmol) was added as an internal standard for the analysis by $^1$H NMR; as a result, it was confirmed that pentamethylenediisocyanate as the target compound was produced with the yield of 83%.

Example 24: Synthesis of 1,4-phenylenediisocyanate

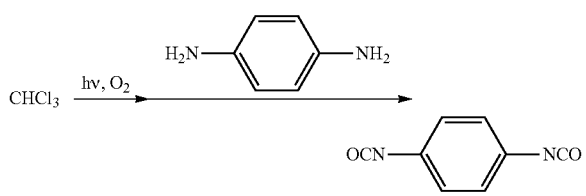

Purified chloroform (50 mL) was added into the reaction vessel of the reaction system used in Example 1, and oxygen gas was blown into the stirred chloroform at a flow rate of 0.5 L/min at 0° C. to cause bubbling and a light containing UV-C was irradiated.

The power of the low pressure mercury lamp was turned off after 3 hours, and a chloroform solution (5 mL) of 1,4-phenylenediamine (0.54 g, 5 mmol) was added under illumination of a general room lamp. Then, pyridine (4 mL, 50 mmol) was added, and the mixture was stirred at 0° C. for 30 minutes. To the reaction mixture, 1,2-dichloroethane (395 µL, 5 mmol) was added as an internal standard for the analysis by $^1$H NMR; as a result, it was confirmed that 1,4-phenylenediisocyanate as the target compound was produced with the yield of 47%.

EXPLANATION OF REFERENCES

1: Light-irradiating means, 2: Jacket, 3: Water bath, 4: Stirring bar, 5: Heating medium or Cooling medium, 6: Cylindrical reaction vessel

The invention claimed is:

1. A method for producing an isocyanate compound, the method comprising the steps of:
    irradiating a high energy light to a halogenated methane at a temperature of 15° C. or lower in the presence of oxygen, and
    adding a primary amine compound to be reacted without irradiating a high energy light.

2. The method for producing the isocyanate compound according to claim 1, wherein the temperature is 5° C. or lower.

3. The method for producing the isocyanate compound according to claim 1, wherein a base is added in addition to the amine compound.

4. The method for producing the isocyanate compound according to claim 3, wherein the base is an organic base.

5. The method for producing the isocyanate compound according to claim 4, wherein the organic base is one or more heterocyclic aromatic amines selected from pyridine, picoline and lutidine.

6. The method for producing the isocyanate compound according to claim 4, wherein the organic base is one or more non-nucleophilic strong bases selected from 1,5,7-triazabicyclo[4.4.0]dec-5-ene, 7-methyl-1,5,7-triazabicyclo[4.4.0]dec-5-ene, 1,8-diazabicyclo[5.4.0]undec-7-ene, 1,5-diazabicyclo[4.3.0]non-5-ene and 1,1,3,3-tetramethylguanidine.

7. The method for producing the isocyanate compound according to claim 1, wherein the high energy light comprises a light having a wavelength of 180 nm or more and 280 nm or less.

8. The method for producing the isocyanate compound according to claim 1, wherein a halogeno group in the halogenated methane is one or more halogeno groups selected from chloro, bromo and iodo.

9. The method for producing the isocyanate compound according to claim 8, the halogenated methane is chloroform.

10. A method for producing a polyurethane, the method comprising the steps of:
    producing a polyisocyanate compound having two or more isocyanate groups by the method according to claim 1, and
    adding a polyol compound to a reaction mixture of the above step comprising the polyisocyanate compound.

\* \* \* \* \*